United States Patent [19]

Aizu et al.

[11] Patent Number: 5,116,116
[45] Date of Patent: May 26, 1992

[54] OPHTHALMOLOGICAL DIAGNOSIS METHOD

[75] Inventors: Yoshihisa Aizu, Machida; Kohji Ogino, Hino, all of Japan

[73] Assignee: Kowa Company Ltd., Japan

[21] Appl. No.: 489,284

[22] Filed: Mar. 5, 1990

[30] Foreign Application Priority Data

| Mar. 6, 1989 | [JP] | Japan | 1-51955 |
| Mar. 6, 1989 | [JP] | Japan | 1-51956 |
| Mar. 6, 1989 | [JP] | Japan | 1-51957 |

[51] Int. Cl.⁵ .............................................. A61B 3/10
[52] U.S. Cl. ................................... 351/221; 351/206; 356/39
[58] Field of Search ................ 351/206, 211, 221; 356/28, 28.5, 39; 128/691

[56] References Cited

U.S. PATENT DOCUMENTS

| 4,166,695 | 9/1979 | Hill et al. | 356/39 |
| 4,402,601 | 9/1983 | Riva | 351/221 |
| 4,848,897 | 7/1989 | Aizu et al. | 351/221 |

Primary Examiner—Paul M. Dzierzynski
Attorney, Agent, or Firm—Bruce L. Adams; Van C. Wilks

[57] ABSTRACT

An ophthalmological diagnosis method is provided in which a laser beam is projected at a region of the eye fundus to produce a laser speckle pattern formed by light scattered from tissues of the eye fundus. Movement of the speckle pattern is detected to produce a speckle signal which is photon-counted as photoelectric pulses per unit sampling time. The counted data are stored in a computer memory as time series data over one measurement time. The stored data are then processed to provide a correlation function using different delay times and are also divided per unit time. For the divided data, the correlation function or variance is calculated for each unit time. Such an arrangement makes it possible to accomplish accurate evaluation even when there is movement of the eye fundus and thus ensures that measurement data are fully utilized to provide accurate ophthalmological diagnosis.

8 Claims, 8 Drawing Sheets

OPHTHALMOLOGICAL DIAGNOSIS METHOD

BACKGROUND OF THE INVENTION

1. Field of the Invention

This invention relates to an ophthalmological diagnosis method, particularly to an ophthalmological diagnosis method in which a laser beam of a prescribed diameter is used to illuminate the eye fundus and to produce a laser speckle pattern formed by the light scattered by blood cells in the tissues of the eye. A small, circular detecting aperture of a prescribed diameter is used to detect movement of the laser speckle pattern at an observation plane as fluctuations in the speckle light intensity, and the photon correlation function thereof is measured to determine the state of the blood flow in eye fundus tissues.

2. Description of the Prior Art

Conventional laser Doppler methods of measuring blood flow in retinal and other tissue by illuminating the eye fundus with a laser beam include those described in "Investigative Ophthalmology," vol. 11 No. 11, p936 (November 1972) and "Science," vol. 186 (November 1974) p830, and in Japanese Unexamined Patent Publication Nos. 55-75668, 55-75669, 55-75670, 52-142885 (corresponding to GB 13132/76 and U.S. Pat. No. 4,166,695), 56-125033 (corresponding to GB 79/37799), 58-118730 (corresponding to U.S. Pat. No. 4,402,601) and U.S. Pat. No. 4,142,796. However, these laser Doppler methods involve the use of a high precision optical system, are complicated to use and provide results which lack repeatability and reliability, which hinder the practical utilization of the method.

In order to overcome the aforementioned drawbacks the present inventors have adapted laser speckle methods used for blood flow measurement in skin and the like (such as the methods described in Japanese Unexamined Patent Publication Nos. 60-199430, 60-203235 and 60203236 and in "Optics Letters," vol. 10 No. 3 (March 1985) p104) for ophthalmological applications involving evaluating the state of the blood flow in tissues of the eye fundus, and have filed the following related patent applications: Japanese Unexamined Patent Publication Nos. 62-275431 (U.S. Pat. No. 4,734,107 and EPC 234869), 63-238843 (EPC 284248) and 63-242220 (EPC 285314).

In the methods described in these publications with respect to eye fundus measurements, a detecting aperture is used to extract time-base fluctuations in the intensity of speckles formed at an optical Fourier Transform plane with respect to the eye fundus, or at the Fraunhofer refraction plane, or at an image plane (or a magnified image plane) that is conjugate with respect to the eye fundus.

There is the necessity of projecting a laser beam as weak as possible in a short time for safety reasons. This results in the detection of a very weak intensity of light, thus needing a photon correlation method for correlation computation which uses a digital correlator to count photoelectric pulses in order to evaluate the blood flow state. In this case, measurement is made not only for a normal blood flow, but also for an abnormal fast or slow blood flow appearing in diseased eyes. The blood flow in the eye fundus also depends on a spot to be measured and on the patient to be examined. Thus, extraction of a good correlation curve greatly depends on how the sampling time $\Delta t$ is set which determines a time resolution in carrying out the correlation calculation.

The digital correlator which has been used so far computes correlation data with a predetermined sampling time $\Delta t$, and thus cannot reconstruct the correlation data with a different sampling time $\Delta t$. This necessitates renewed sampling of data. Usually, it is hard to exactly evaluate which sampling time $\Delta t$ is suitable for obtaining the correlation function before measurement is initiated. The sampling time must usually be changed every day depending on intended use. Thus, the repeated sampling of data burdens the patients and disadvantageously consumes time.

If a correlation curve indicates that the object has high and low frequency components, there further would occur a problem in the case where the evaluation is performed
with the sampling time $\Delta t$ which is more suitably applicable for either one of the frequency components. This means that the measurement must be repeated with a different sampling time each time.

Furthermore, when a time change in blood flow at a certain time is to be observed, it is necessary to perform measurement at a sub-divided time. In this case, measurement data sampled at the sub-divided time are stored for analysis upon completion of measurement and measurement is then again initiated after completion of analysis. This results in intermittent and inaccurate measurement. The sub-division of the measurement time may thus be dependent on intended use.

On the other hand, as described in Japanese Unexamined Patent Publication No. 63-242220 (EPC 285314), the blood flow in a single specific blood vessel may be evaluated by detecting the speckle pattern on the image plane. In the method thus described, a detecting aperture is aligned with the image of the blood vessel of interest on a magnified image plane and time-course fluctuations in speckle light intensity at that image plane are extracted to obtain a speckle signal. With this arrangement, a frequent occurrence during the measurement procedure is that the fundus image moves out of alignment on the detection plane owing to any of a number of factors including eye movement, vibration and misalignment between the apparatus and the eye. This will often result in obstruction by the wall of the blood vessel or the intrusion of a different blood vessel into the detection zone. In a clinical context, these are major problems which are constantly encountered, especially when the eye is inadequately fixed or when the patient is particularly apprehensive.

A look at the correlation functions of signals obtained from a single measurement shows that the signals include various components, which has an adverse effect on the repeatability of blood flow measurements. Also, since it is unclear which components are not required or to what extent the inclusion of a particular component contributes to the end result, an attempt to extract the original blood flow signal by removing unnecessary components from a correlation function curve based on data from one measurement is an impracticably difficult task. In addition, a blink of the eye during the measurement process or the intrusion of noise or an undesired signal can make an entire set of correlation data obtained during a measurement session unusable for the purposes of accurate evaluation, requiring that the measurement be redone from the beginning.

SUMMARY OF THE INVENTION

It is therefore an object of the present invention to provide an ophthalmological diagnosis method capable of ensuring the secure acquisition of correlation data and accurate ophthalmological diagnosis.

According to the present invention there is provided an ophthalmological diagnosis method comprising the steps of projecting a laser beam of prescribed diameter at a region of the eye to produce a laser speckle pattern formed by light scattered from tissues of the eye fundus; photoelectrically detecting movement of the laser speckle pattern through a detecting aperture as fluctuation in the light intensity of the speckles to produce a speckle signal corresponding to the detected movement; measuring the photon correlation function of the speckle signal to determine the blood flow state in the eye fundus tissue from the measured photon correlation function; and photoelectrically counting detected output signals as photoelectric pulses per unit sampling time. In such an arrangement, the counted data are stored in a computer memory as time series data over one measurement time, and a correlation function is calculated for the stored data.

In the basic embodiment of this invention, low intensity speckles from the eye fundus are detected as photoelectric pulse signals and these time series pulses are counted at prescribed sampling times and the count values are stored in a memory. Upon completion of the measurement, the count values are read out and evaluated for correlation. This advantageously enables repeated use of measured data. Preferably, the correlation function is calculated for the stored data with at least different delay times, thereby making it possible to evaluate the measured data with different delay times.

In another embodiment, the data stored in the memory is sub-divided per unit time and the count data are processed to provide a correlation function, correlation time or variance for each unit time. The measured data are grouped according to the calculated correlation time or variance. This serves to determine whether the signal concerned came from a blood vessel or from surrounding tissue, or whether it is of indeterminate origin, and the signals are then grouped accordingly and subjected to final evaluation.

This enables the signals to be evaluated individually without the inclusion of different signal components, thereby making it possible to extract signals specifically produced by a blood vessel. This thus makes it possible to accomplish accurate evaluation even when there is movement of the eye fundus and thus ensures that measurement data are fully utilized. A further advantage of the method is that it can be extended to the evaluation of the state of the blood flow in the capillaries of surrounding tissue or in choroid layers.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

The invention will now be described in detail with reference to the embodiments shown in the drawings. The invention is concerned specifically with the fundus region of the eye, and as such the following description relates to when an eye fundus camera is used to measure blood flow in the eye fundus.

Figure 1:
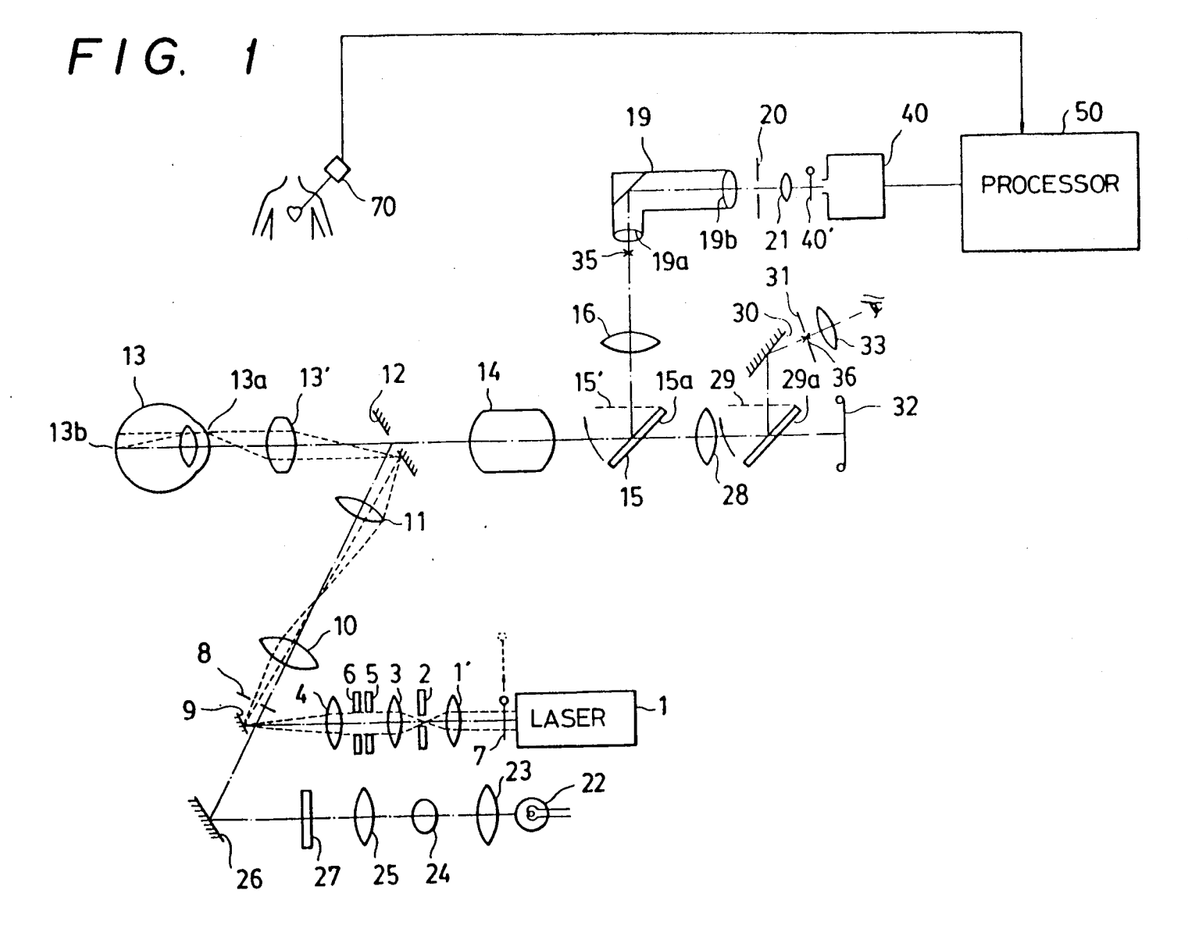
FIG. 1 is a schematic diagram of the arrangement of a first embodiment of an apparatus employing the method of the invention.

FIG. 1 shows an overall schematic view of an apparatus for carrying out the measurement method according to the present invention. A laser beam such as from a red-light He-Ne (wavelength: 632.8 nm) type laser beam source 1, for example, passes through a condenser lens 1' and a light quantity adjustment filter 2 for adjusting the intensity of the beam. The beam then passes through relay lenses 3 and 4 and enters the eye fundus illuminating projector of an eye fundus camera.

Figures 2, 3, 4:
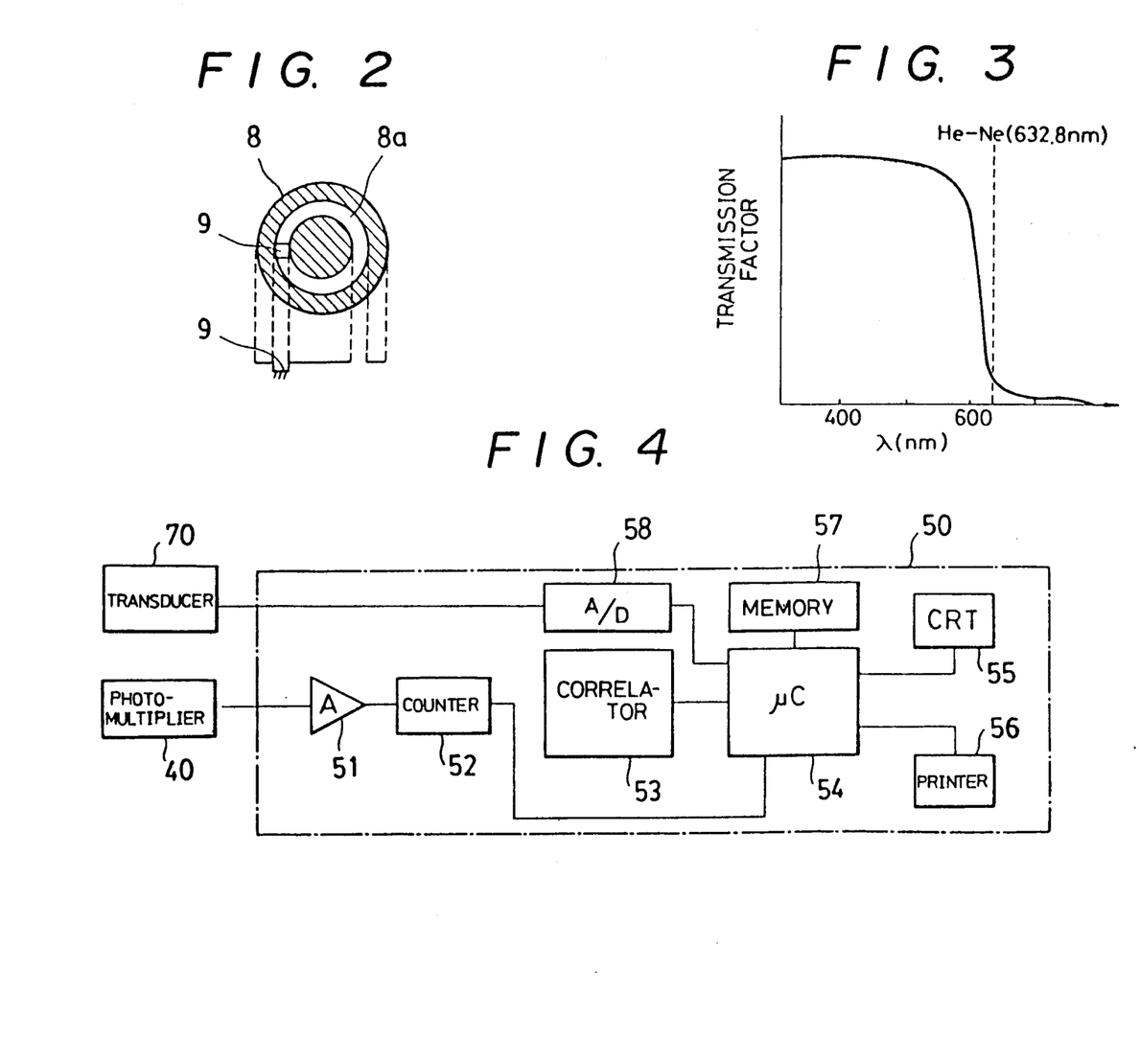
FIG. 2 is a diagram showing the structure of a ring slit.
FIG. 3 is a characteristic curve showing the characteristics of a wavelength separation filter used in the embodiment of FIG. 1.
FIG. 4 is a block diagram showing the arrangement of a signal processor used in the embodiment of FIG. 1.

Two stops 5 and 6 are disposed between the relay lenses 3 and 4 for selectively adjusting the size and shape of the region of the eye fundus irradiated by the laser beam. Disposed near the beam-emitting end of the laser beam source 1 is a shutter 7 which can be opened or closed as required. As shown in FIG. 2, the laser beam issuing from the relay lens 4 is reflected by a mirror 9 provided in one portion of an annular aperture 8a formed in a ring slit 8 disposed in the eye fundus illuminating projector, so that the reflected laser beam travels along the same light path to the eye fundus as that followed by the beam of light directed into the eye fundus to provide illumination for photography and observation. As a result, the laser beam passes through relay lenses 10 and 11, is reflected by a ring mirror 12, is converged on the cornea 13a of the eye under examination 13 by an objective lens 13' and then diverges at the eye fundus 13b to thereby form a projected region which is larger than the diameter of the blood vessel of interest.

This area is also illuminated by the illuminating projector of the fundus camera, facilitating observation. The system which provides the illumination for observation is constituted of an observation light source 22, a condenser lens 23, a condenser lens 25, a filter 27 and a mirror 26 disposed on the same light path as a photographic light source 24. As the path of the laser beam coincides with that of the beam of photographic and observation light, the laser beam can be made to impinge on the desired region of the eye fundus 13b by mechanisms for swinging and tilting the eye fundus camera vertically and horizontally and also by use of the eye fixation means.

The filter 27 disposed between the condenser lens 25 and the mirror 26 is a wavelength separation filter with the characteristics shown in FIG. 3, thereby filtering out red components from the observation and photographic light.

Speckle light produced by the scattering of the laser beam from blood cells moving in the blood vessels in the eye fundus enters the objective lens 13', passes through the ring mirror 12 and then through a photographic lens 14 to impinge on a wavelength separation mirror 15. Like the filter 27, the wavelength separation mirror 15 exhibits the type of spectral characteristics illustrated in FIG. 3, and since it therefore reflects most of the red light components and transmits other light, it reflects most of the speckle light (red) generated by the He-Ne laser beam. A lens 16 forms the reflected light into an image at an image plane 35 and is then magnified by an objective lens 19a and eyepiece lens 19b of a microscope optical system 19. The magnified image passes through a detecting aperture 20, is converged once again by a condenser lens 21 and detected by a photomultiplier 40. A shutter 40' is disposed in front of the photomultiplier 40 and the output signal obtained from the photomultiplier 40 when this shutter is open is input to a signal processor 50.

As shown in FIG. 4, the signal processor 50 is constituted of an amplifier 51, photon counting unit 52, a correlator 53, a microcomputer 54, a CRT display 55, a printer 56 and a memory 57.

The light passing through the wavelength separation mirror 15 advances through a relay lens 28, is reflected by a swingable mirror 29 and a mirror 30, and is then directed, via a reticle 31, to an eyepiece 33 through which it can be observed or recorded on a photographic film 32.

With the apparatus arranged as described, after the power has been turned on and the patient positioned, the eye fundus 13b of the eye 13 under examination is observed by means of the observation light optical system constituted by the elements 22 to 26. The laser light beam source 1 is then activated. At this point the filter is used to adjust the light output to the level used for system set-up and the stops 5 and 6 are used to set the size and shape of the region illuminated by the laser beam. Next, the shutter 7 is opened and, after the measurement position has been set, the speckle pattern is confirmed by means of the observation light optical system constituted by the elements 28 to 31.

With respect to this embodiment, to facilitate the laser beam projection, the size of the region of the eye fundus 13b projected by the laser beam at the portions at which measurement is to be carried out is made larger in diameter than the blood vessel, such as a diameter of 1 mm to 3 mm. This may therefore result in the inclusion of a plurality of relatively thick blood vessels in addition to capillaries. If the detection is made at the Fourier plane relative to the eye fundus, the rays of light scattered from all the illuminated regions are superimposed with the result that the analysis based on the speckles indicates an overall evaluation of a state of blood flow for all the blood vessels included in the illuminated region. It is thus recommendable to detect the speckle pattern at a magnified image plane as shown in FIG. 1 if the blood flow of a specific blood vessel is to be measured.

It is, however, needless to say that the invention is applicable to detection at both of the Fourier transform plane (Fraunhofer refraction plane) and image plane (magnified image plane). The following description will be made with reference to the detection at the image plane.

To measure the blood flow in a specific blood vessel, the blood vessel to be measured is selected at the magnified image plane and the detecting aperture 20 is then located within the blood vessel image at the magnified image plane. Thus, a conjugate image of the eye fundus is formed at the image plane 35 shown in FIG. 1 and the image is then magnified by the objective lens 19a and eyepiece lens 19b of the microscope optical system 19, and fluctuations in the intensity of the speckle light are detected by the detecting aperture 20 disposed at the magnified image plane. The light is then converged by a condenser lens 21 and converted into a electrical signal by the photomultiplier 40, the shutter 40' being in the open position.

The output produced by the photomultiplier 40 during measurement constitutes a speckle signal which varies with time in accordance with the movement of the blood cells. This speckle signal is amplified by the amplifier 51 in the signal processor 50, and by means of the photon counting unit 52, time series data of the photoelectric pulses corresponding to the intensity of the light are counted per set time and the count values are stored sequentially in the memory 57. After the measurement is completed the data are read out of the memory 57, the photon correlation function is calculated by the correlator 53 and the results of the analysis and evaluation are output to the CRT display 55 and/or to the printer 56. This control sequence is executed by the microcomputer 54.

As thus described in the foregoing, since in accordance with this embodiment the detecting aperture 20 is disposed at the magnified image plane, the blood flow in a specific single blood vessel can be measured by selecting the blood vessel in the region by the laser beam and locating the detecting aperture 20 within the blood vessel image, either by adjusting the position of the detecting aperture 20 or by adjusting the fixation of the eye under examination 13.

Figure 5:
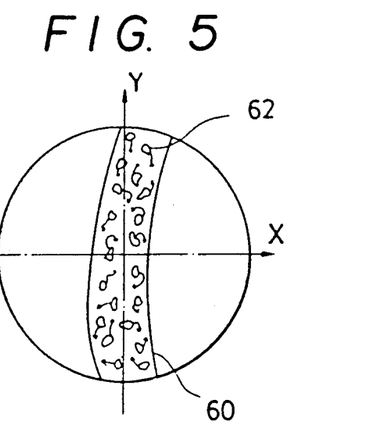
FIG. 5 is a diagram showing image plane speckles observed at the detecting aperture plane.

The detecting aperture 20 may be a pinhole. A magnified image of a desired single blood vessel 60 such as that shown in FIG. 5 can be observed. If a pinhole such as the pinhole 61 shown in FIG. 6 having a smaller diameter than that of the observed blood vessel image is disposed at a portion where the image plane speckles within the blood vessel are in motion, speckles passing across the detecting aperture 20 will give rise to a corresponding fluctuation in the intensity of the detected light, thereby producing a speckle signal.

Figure 6:
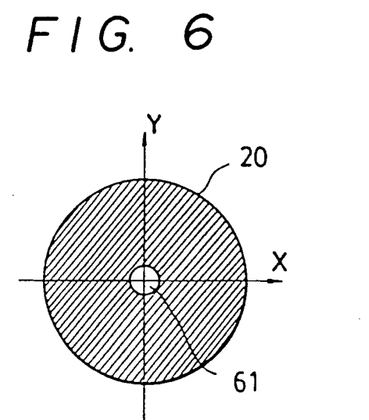
FIG. 6 is a diagram of a detecting aperture.

It is observed that speckles 62 produced by in vivo tissue exhibit a characteristic boiling motion caused by multiple scattering. Unlike translational motion, which is observed when image plane speckles 62 move in one direction without any change, boiling motion refers to what appears as a random, flickering motion of the image plane speckles 62, which ceaselessly change in intensity. It is, however, needless to say that speckle signals can also be derived from such speckles exhibiting fluctuation in intensity at the pinhole 61.

Figure 7:
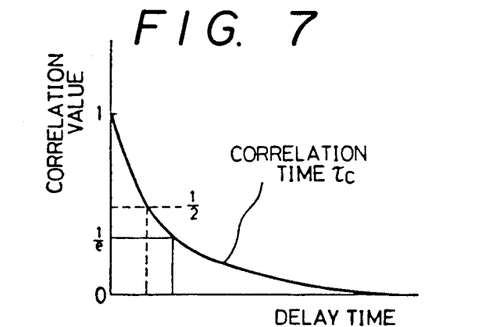
FIG. 7 is a graph showing the relationship between time delay and correlation time.
Figure 8:
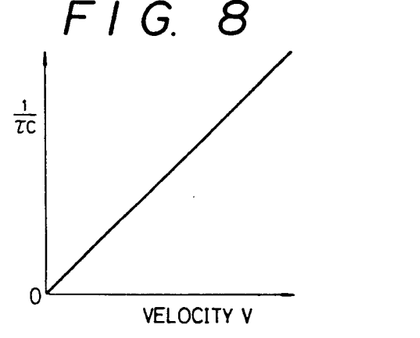
FIG. 8 is a graph showing the relationship between velocity and correlation time.

As the rate at which image speckles 62 traverse the aperture changes in proportion to the velocity of the blood flow, an increase in the velocity of the blood flow produces a corresponding increase in the rate at which the speckle signal varies with time, which increases the high frequency component of the signal. After the autocorrelation function of the signal is obtained with the signal processor 50, the degree of attenuation is evaluated in accordance with the correlation time. If, as shown in FIG. 7, correlation time $\tau c$ is taken as the time delay for the correlation value to become 1/e (or ½ or the like), the relationship between the inverse thereof $1/\tau c$ and image plane speckle velocity will be linear. As the fluctuation velocity of the image plane speckles 62 directly reflects blood flow velocity, blood flow velocity V can be evaluated from $1/\tau c$ from the relationship shown in FIG. 8.

In the signal processor 50, a time series pulse signal (FIG. 9b) obtained from the photon counting unit 52 is converted to a pulse train signal (FIG. 9a) at a density that is proportional to the speckle signal intensity. Storing each of these in memory is impractical as it would require a very large memory capacity and also owing to the high speed response requirements of the processing system.

Figure 9:
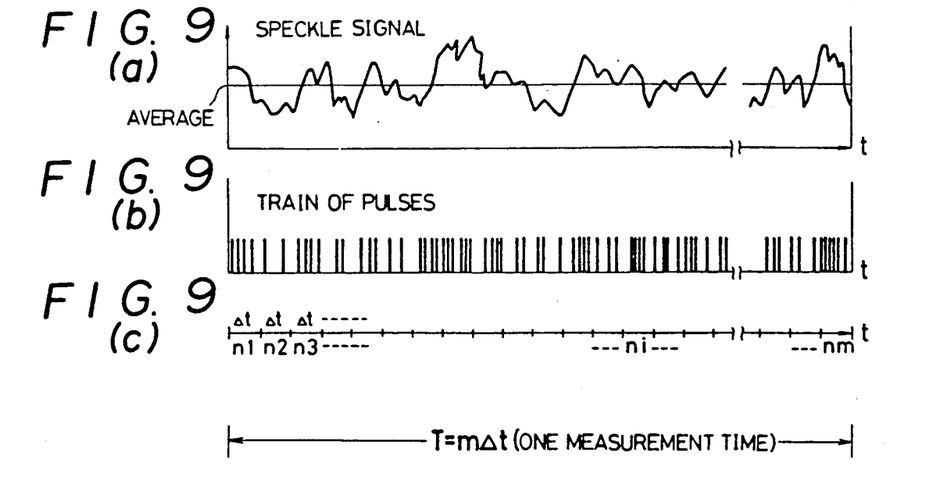
FIGS. 9a to 9c are speckle signal sampling waveforms.

Therefore, in this embodiment, as shown in FIG. 9c, pulses are counted at each prescribed sampling time $\Delta t$ and the corresponding count values are stored in memory as n1, n2, n3, ... ni ... nm. Hence, in one measurement time T, m samplings are performed and m data are stored in memory. Thus, $T=m\Delta t$. $\Delta t$ preferably is set at a measurable time, which is obtained by sufficiently dividing the shortest value $\tau cmin$ for the time correlation length $\tau c$ of the signal to be measured. If for example $\tau cmin = 20$ microseconds, then the setting would be $\Delta t \leq 0.5-1$ microseconds. This means that $\Delta t$ forms the minimum time unit, and as such determines the time resolution of the measurement.

Figure 10A:
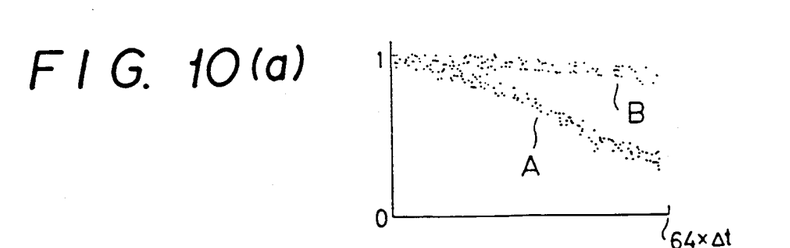
FIGS. 10a to 10b are graphs each showing a correlation data with different delay times.
Figure 10B:
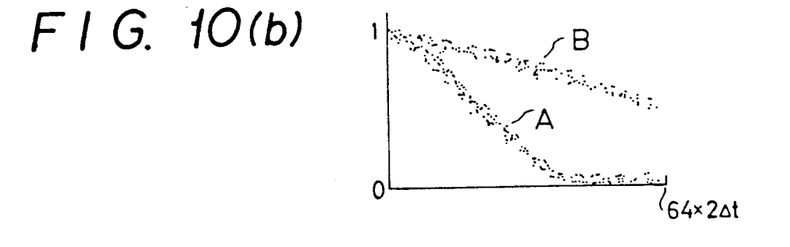
Figure 10C:
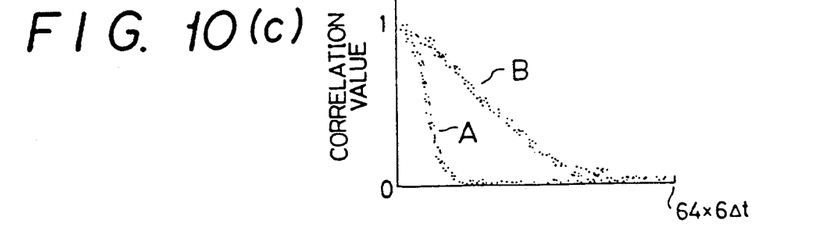

After completion of measurement, the stored data n1, n2, n3, ... are read out and processed for correlation calculation by the correlator 53. At this time, the delay time $\Delta \tau$ is for one channel of the correlation calculation and is so set as to be a positive integer multiple of the sampling time $\Delta t$. FIG. 10a shows the 64-channel correlation calculation with $\Delta \tau = \Delta t$ with two different correlation data A and B being plotted together. This indicates that no $\tau c$ evaluation is possible with respect to the data B because of too short delay time $\Delta \tau$. FIG. 10b shows the correlation curve with $\Delta \tau = 2\Delta t$ and FIG. 10c with $\Delta \tau = 6\Delta t$. For the example as shown in FIG. 10c, both of the data A and B are properly evaluated and can be subjected to comparison. Thus, the measurement data can advantageously be evaluated for correlation repeatedly with different delay times if they are stored. It will be understood that, in the clinical diagnosis, it is very important to store the data in the memory because it is difficult to measure the data repeatedly.

Figure 11A:
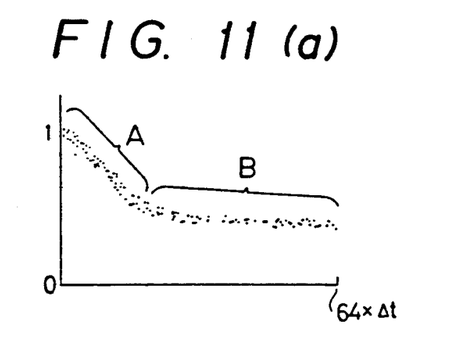
FIGS. 11a to 11b are graphs each showing a correlation data with a portion thereof evaluated with a different delay time.
Figure 11B:
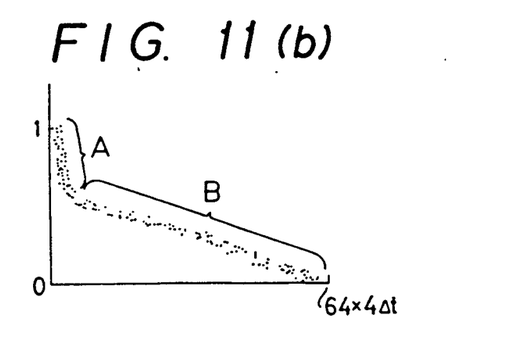

FIG. 11a shows correlation data with $\Delta \tau = \Delta t$ with a portion of A assuring good evaluation and a portion of B indicating unclear components. The evaluation with $\Delta \tau = 4\Delta t$ makes the portion B clearer as shown in FIG. 11b, but causes a shift in the portion A to the left with the result of no sufficient evaluation. This, however, means that use of different delay time $\Delta \tau$ depending on the data contained in the correlation function advantageously enables separate evaluation for each component. It is thus very preferable, particularly when the blood flow in the eye fundus includes the retinal blood flow and also other components based on eye movement or the blood flows in choroid layers. It is to be noted that it cannot be certainly identified whether the portion B in FIG. 11b is related to noise or other signal components.

Figure 12A:
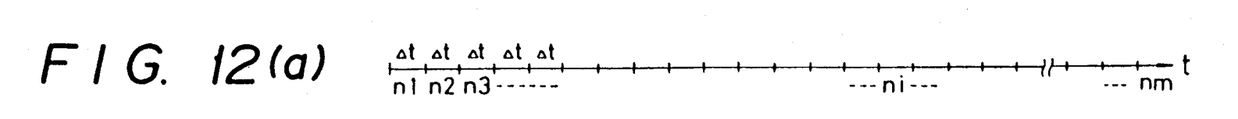
FIGS. 12a to 12e are signal waveforms illustrating the calculation of correlation time in measurement time divisions.
Figure 12B:
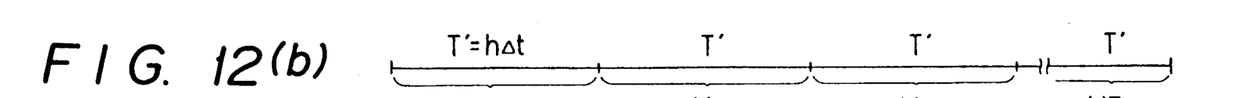

As shown in FIGS. 12a and 12b, measurement time T is divided into m/h equal parts, with each time division $T' = h\Delta t$ being constituted of unit times U1, U2, U3, ..., Um/h. And for each unit time, the correlation function is obtained with the same delay time $\Delta \tau$ for all the unit times or with an appropriate delay time set separately depending on the unit time. This enables evaluation of a time-course change in the blood flow per time $T' = h\Delta t$ obtained by dividing the measurement time T into m/h equal parts. A very short time $T' = h\Delta t$, however, guarantees no sufficient convergence of correlation function in each unit time, so that $\Delta t < < T'$ is required. On the other hand, too few divisions with T' being near T are meaningless. Therefore, a condition $T' < T/10$ ( $m/h \leq 10$) is preferable. Note that the number of division 5 m/h is changeable and can be set to be optimum. If abnormal data occur because of eye blinking, only the unit time including the abnormal data can be excluded from evaluation.

Figure 12C:
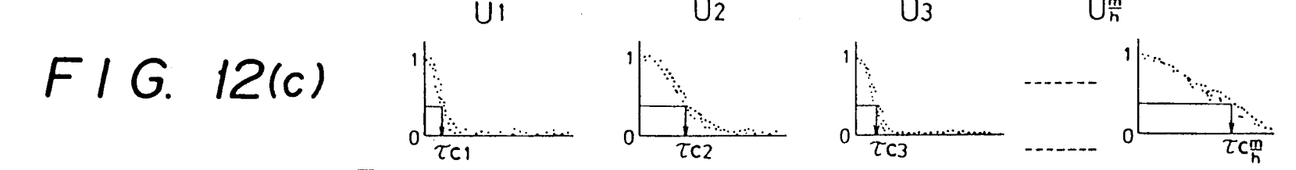
Figure 12D:
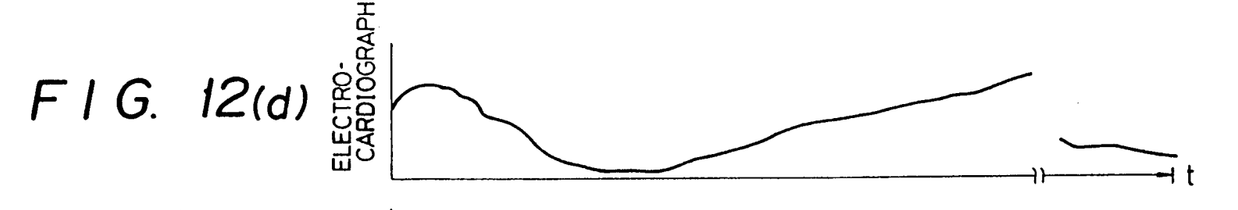
Figure 12E:
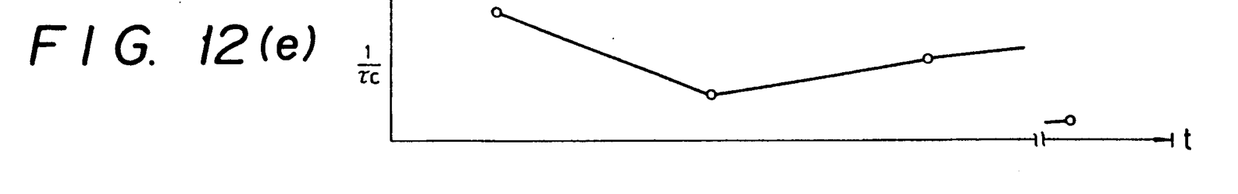

The correlation function per unit time is thus obtained as shown in FIG. 12c and then subjected to a smoothing process to provide correlation times $\tau c1, \tau c2, \tau c3, ... \tau cm/n$, the inverse of which is plotted as shown in FIG. 12e. At the same time, electrocardiographic data of the patient are detected using an electrocardiograph transducer 70 in FIG. 1 and applied to the analog-digital converter 58 for conversion into digital signals, which are then processed in the computer 54 and stored in the memory 57. FIG. 12d shows such electrocardiographic data, which are plotted on the same time scale as FIG. 12e showing the inverse of the correlation time. This provides useful means for evaluating a flow due to heart pulse. The data in FIG. 12e can be displayed again with the different number of on the same time scale as in FIG. 12d.

Figure 13:
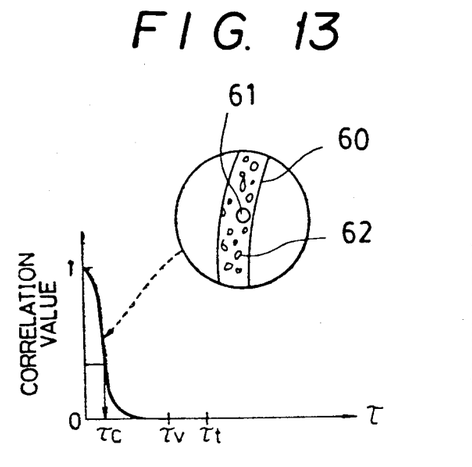
FIGS. 13 and 14 are characteristic curves of the correlation function between blood vessels and the surrounding tissue.
Figure 14:
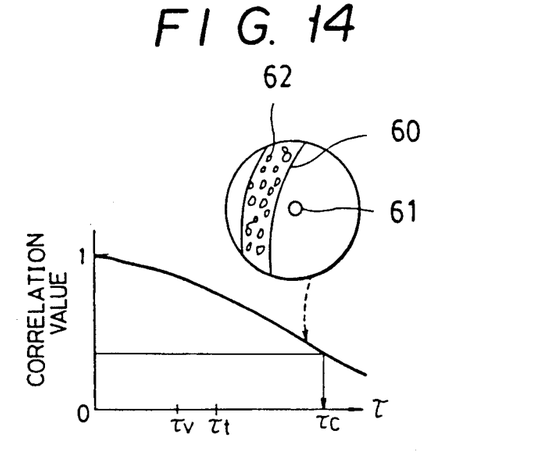

When a blood vessel signal is being measured, there is an increase in speckle velocity and a decrease in the value of $\tau c$, as shown in FIG. 13. This means that the signal contains many high frequency components. On the other hand, as illustrated by FIG. 14, a signal from the surrounding tissue results in a low speckle velocity and a longer $\tau c$, which signifies the inclusion of many low frequency components.

Figure 15:
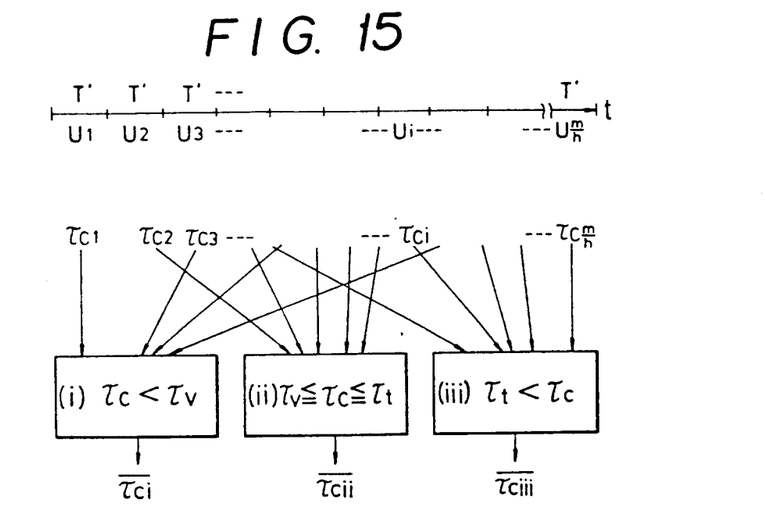
FIG. 15 is an explanatory diagram illustrating the use of comparison to sorted correlation time into groups.

Two threshold values $\tau v$ and $\tau t$ are set, based on correlation values of typical blood flow and surrounding tissue signals. The threshold values are statistically determined and may be changeable if necessary. Each correlation time $\tau c$ per unit time is sequentially sorted into one of three groups, group (i) $\tau c < \tau v$, group (ii) $\tau v \leq \tau c \leq \tau t$, and group (iii) $\tau t < \tau c$ as shown in FIG. 15. Then, the average of the correlation time $\tau c$ per group is calculated. It can be evaluated that the group (i) having the correlation time $\overline{\tau ci}$ indicates blood vessel signal data, group (ii) having $\overline{\tau cii}$ indeterminate signal data, and group (iii) having $\overline{\tau ciii}$ surrounding tissue signal data.

Therefore, even if the blood vessel of interest moves out of alignment during measurement, only the data which are being measured can be used to distinguish and extract data derived from blood vessel portions, enabling the blood vessel data of interest to be reconstructed and evaluated. As such, the method offers a high level of efficiency with respect to clinical measurements. Moreover, sorting data signals from the vicinity of blood vessel walls into group (ii) prevents measured data from such slow-blood-flow areas being evaluated in group (i). If on the other hand it is desirable that such components be included in group (i) for the purposes of an overall evaluation, this too can be accomplished by raising the threshold value $\tau v$.

This method therefore enables data which are clearly anomalous, such as data produced by the blinking of the eye or by extraneous noise, to be excluded from group (i). Since data of group (iii) can also be used to evaluate blood flow states in capillaries, choroid layers and the like, as a whole all of the data can be utilized effectively. In addition, as evaluation is still possible even when the part concerned moves, fewer repeat measurements are required.

Instead of calculating the average of the correlation time $\tau c$ per group, the n original count data in all the units belonging to the group (i) can be concatenated into time series and be smoothed to provide a correlation time $\tau ci$. The same process can also be applied for the groups (ii) and (iii) to provide correlation times $\tau cii$ and $\tau ciii$.

Figure 16:
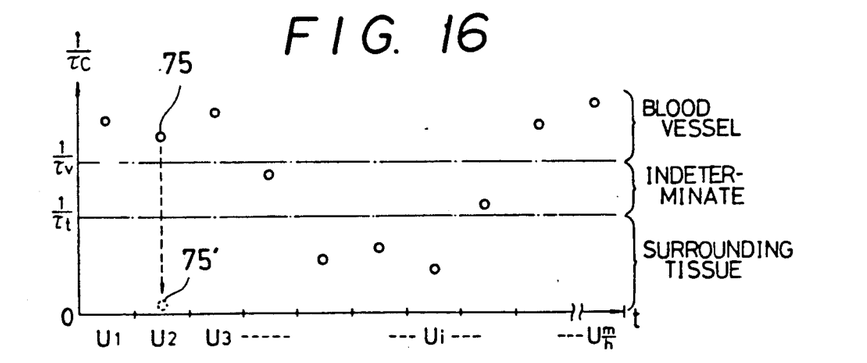
FIG. 16 is a characteristic curve showing the inverse of the correlation time relative to time.

The inverse of the correlation time per unit time as obtained from FIGS. 15 can be plotted relative to a time axis as in FIG. 16 together with an indication of threshold values $1/\tau v$ and $1/\tau t$. Thus, the range $1/\tau c \geq 1/\tau v$ indicates blood vessel signals, $1/\tau v \geq 1/\tau c \geq 1/\tau t$ indeterminate signals and $1/\tau t \geq 1/\tau c$ surrounding tissue signals. This facilitates the observation when there is a deviation from (and a return to) a blood vessel during measurement. Thus, this provides a clear understanding of the nature of time series fluctuations in the measured data.

In FIG. 16, data 75 is shown as representing blood vessel signal data. Assume that at this point there had been a variation to data 75' signifying a surrounding tissue signal In view of the fact that data 75 (75') is immediately preceded and followed by $1/\tau c \geq 1/\tau v$ data and it is hardly likely that there was a blood vessel deviation only within unit U2, the evaluation can be supplemented by the judgment that the data 75' was based on a measurement anomaly caused by a blink or the intrusion of noise. The ability to use FIG. 16 to determine whether a time series change in measured data is systematic or not is of considerable value.

As a special example of the above method, the threshold value $\tau v$ is made equal to $\tau t$ and the data is arranged into two groups, for example $\tau c < \tau v = \tau t$ and $\tau c > \tau v = \tau t$. By eliminating group (ii), this simplifies the signal processing but has the drawback of readily giving rise to aberration in the measurement of borderline data. However, this can be disregarded when there are large quantities of data.

The data of FIG. 16 is also worth studying for what it can reveal concerning eye movement. Specifically, it can be used to estimate the velocity of eye movements and to compare the motion of a deviation from a blood vessel with the motion of a shift back to the blood vessel.

The stored data per unit time can also be processed to provide a variance. This will be described more fully.

Figures 17A, 17B, 17C:
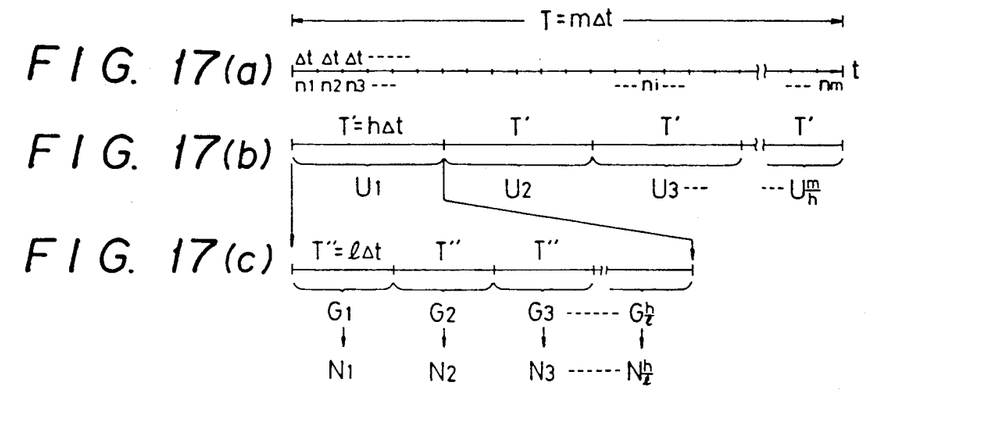
FIGS. 17a to 17c are signal waveforms illustrating the calculation of data variance in measurement time divisions.

As shown in FIG. 17a, measurement time T is divided into m/h equal parts, with each time division $T' = h\Delta t$ being constituted of unit times U1, U2, U3, ..., Um/h, as in FIG. 12b. As illustrated by FIGS. 17b and 17c, each such unit is further subdivided into h/l equal parts, with each time division $T'' = \Delta t$ being constituted of gate times G1, G2, G3, ..., Gh/l. As there are l count data n1, n2, n3, ..., nl in the initial gate time G1, the sum $N_1$ $$\sum_{i=1}^{l} ni$$

is calculated to obtain the total pulse count in G1. The total count n for every $l\Delta t$ data included in each gate time starting from the second also is obtained. Therefore in unit U1 h/l data N1, N2, ..., Nh/l are obtained.

This data is then averaged thus $$\overline{N} = 1/(h/l) \sum_{i=1}^{h/l} Ni$$

and the variance $$<\Delta N^2> = 1/(h/l) \sum_{i=1}^{h/l} (Ni - \overline{N})^2$$

is calculated to obtain the normalized variance $\sigma = <N^2>/\overline{N}$.

Normalized variance $\sigma 1$ is thus determined with respect to the first unit U1, and in the same way, with respect to U2, U3, ..., Um/h, $\sigma 2$, $\sigma 3$, ..., $\sigma m/h$ is obtained to determine the overall number of m/h $\sigma$ values.

Figure 18:
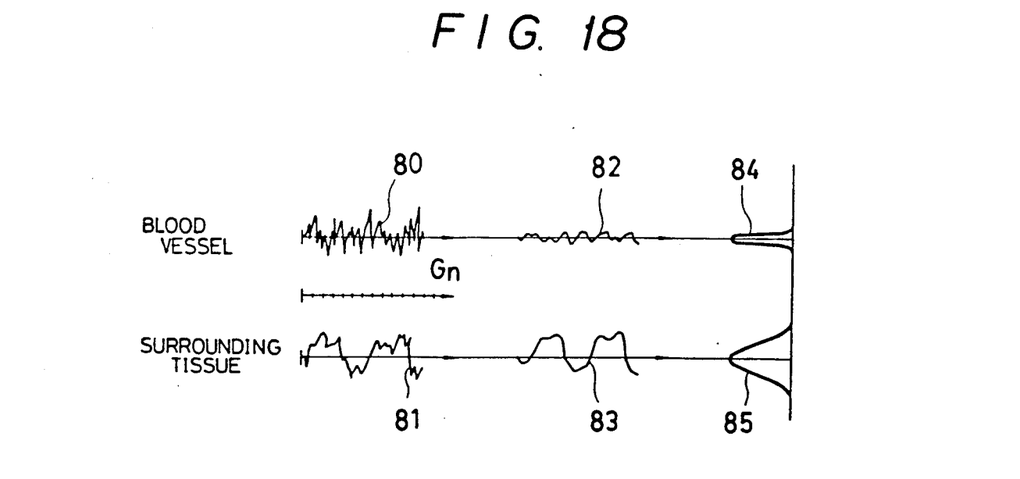
FIG. 18 is an explanatory diagram of the process of establishing variance values of blood vessel signals and surrounding tissue signals.

When count values n per $\Delta t$ are plotted instantaneously, as shown on the left side of FIG. 18, a blood vessel signal 80 shows a rapid fluctuation relative to time, while in the case of a surrounding tissue signal 81 the fluctuation is relatively slow. If this is plotted using a suitable gate time and a count value N obtained by summing all data gate by gate is plotted, it can be seen that the effect is to smooth the blood vessel signal 82 by reducing the amplitude of the high frequency components. This produces an amplitude probability distribution as indicated by reference numeral 84, which means a decrease in the variance $<\Delta N^2>$.

Owing to the predominance of low frequency components, surrounding tissue signals continue to have a portion of high amplitudes shown in the curve 83, resulting in a distribution indicated by reference numeral 85 and a larger variance than that of the blood vessel signal. A blood flow signal can therefore be distinguished from a surrounding tissue signal by comparing the variance values of blood vessel signals and surrounding tissue signals. However, with n and N being pulse count values, the larger the light quantity, the larger the absolute values of these become. This being the case, it is preferable to base evaluations on a variance $\sigma = <\Delta N^2>/\bar{N}$ normalized using an incremented count value $\bar{N}$ per gate time averaged for one unit.

Figure 19:
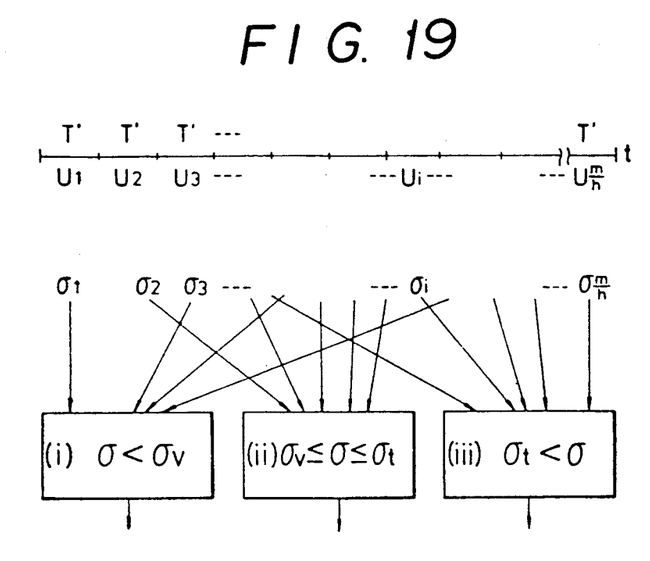
FIG. 19 is an explanatory diagram illustrating the use of comparison to sort variances into groups.

Two threshold values $\sigma v$ and $\sigma t$ are set, based on variance values of typical blood flow and surrounding tissue signals. As shown in FIG. 19, each variance $\sigma$ is sequentially sorted into one of three groups, group (i) $\sigma < \sigma v$, group (ii) $\sigma v \leq \sigma \leq \sigma t$, and group (iii) $\sigma t < \sigma$. Then, based on the order in which the variance values $\sigma$ are sorted ($\sigma 1$ being the first and $\sigma i$ the ith), the original count data items n are concatenated, group by group, into time series. It can be evaluated that the group (i) indicates blood vessel signal data, group (ii) indeterminate signal data, and group (iii) surrounding tissue signal data.

Therefore, even if the blood vessel of interest moves out of alignment during measurement, the $\sigma$ value can be used to distinguish and extract data derived from blood vessel portions, enabling the blood vessel data of interest to be reconstructed and evaluated. As such, the method offers a high level of efficiency with respect to clinical measurements. Moreover, sorting data signals from the vicinity of blood vessel walls into group (ii) prevents measured data from such slow-blood-flow areas being evaluated in group (i). If on the other hand it is desirable that such components be included in group (i) for the purposes of an overall evaluation, this too can be accomplished by raising the threshold value $\sigma v$.

This method therefore enables data which are clearly anomalous, such as data produced by the blinking of the eye or by extraneous noise, to be excluded from group (i). Since data of group (iii) can also be used to evaluate blood flow states in capillaries, choroid layers and the like, as a whole all of the data can be utilized effectively. In addition, as evaluation is still possible even when the part concerned moves, fewer repeat measurements are required.

The fact that unit and/or gate times are selectable and also changeable and a computer is used to process data repeatedly to obtain the optimum value for each data item ensures that the evaluation potential of all the data is fully realized.

With reference to the arrangement of data into the groups shown in FIG. 19 borderline data will be uncorrelated. However, owing to the random nature of the speckle signals, similar signal configurations can be correlated as a single train of time series signals without being very much affected by these connecting portions, which is a feature of the invention. In cases where the effect of the uncorrelated portions is large enough to prevent the requisite correlation function from being obtained, a correlation function may be calculated for each unit after data has been grouped as shown in FIG. 19. This involves summing of the correlation data within each group to produce one correlation function for each group which can be used to set correlation times $\tau ci$, $\tau cii$ and $\tau ciii$. In practice, there is little probability of a disorderly exchange of data belonging to group (i) and group (iii). As described below, in most cases changes are logical and systematic, such as from blood vessel to surrounding tissue and back again.

Therefore, even when the data is arranged in the said three groups, each group will seldom be constituted by data from a random plurality of time units. Any such set of data will probably not be drawn from more than two or three time units.

Figure 20:
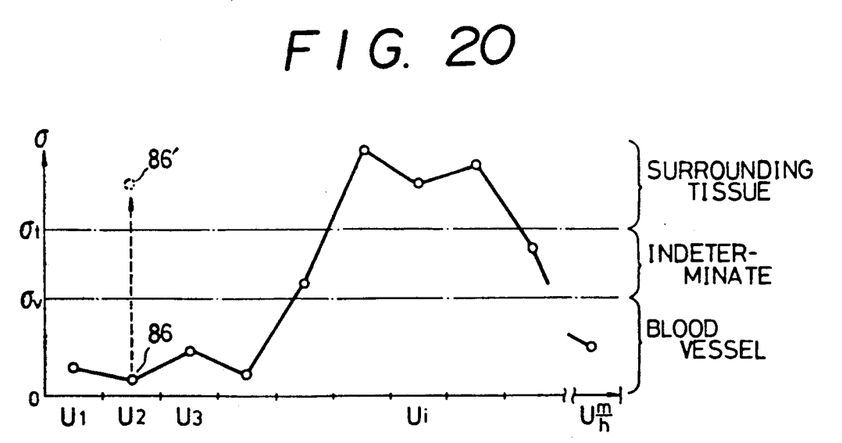
FIG. 20 is a characteristic curve showing variance relative to time.

The variances $\sigma 1$, $\sigma 2$, ..., per unit time as obtained from FIGS. 17 and 19 can be plotted relative to a time axis as in FIG. 20 together with an indication of threshold values $\sigma v$ and $\sigma t$. Thus, the range indicates blood vessel signals, $\sigma v < \sigma < \sigma t$ indeterminate signals and $\sigma t < \sigma$ surrounding tissue signals. This facilitates the observation when there is a deviation from (and a return to) a blood vessel during measurement. Thus, this provides a clear understanding of the nature of time series fluctuations in the measured data.

In FIG. 20, data 86 is shown as representing blood vessel signal data. Assume that at this point there had been a variation to data 86' signifying a surrounding tissue signal. In view of the fact that data 86 (86') is immediately preceded and followed by $\sigma < \sigma v$ data and it is hardly likely that there was a blood vessel deviation only within unit U2, the evaluation can be supplemented by the judgment that the data 86' was based on a measurement anomaly caused by a blink or the intrusion of noise. The ability to use FIG. 20 to determine whether a time series change in measured data is systematic or not is of considerable value.

As a special example of the above method, the threshold value $\sigma v$ is made equal to $\sigma t$ and the data is arranged into two groups, for example $\sigma < \sigma v = \sigma t$ and $\sigma > \sigma v = \sigma t$. By eliminating group (ii), this simplifies the signal processing but has the drawback of readily giving rise to aberration in the measurement of borderline data. However, this can be disregarded when there are large quantities of data.

The data of FIG. 20 is also worth studying for what it can reveal concerning eye movement. Specifically, it can be used to estimate the velocity of eye movements and to compare the motion of a deviation from a blood vessel with the motion of a shift back to the blood vessel.

With respect to correlation computation, the example of FIG. 20 shows that group (i) data are included in both halves of the measurement time period. As an expedient in such a case, by calculating one correlation function, taking the data in the first half as a series, repeating this for the second half, adding the two together and using the result as a blood vessel correlation function and obtaining $\tau ci$, it becomes unnecessary to correlate the data in group (i) on a unit by unit basis.

The range of utility of the invention can be further expanded to include the detection of cardiac functions by using an evaluation procedure in which FIG. 19 is used in concert with an electrocardiograph.

Moreover, it is quite feasible that extensive clinical tests will provide a direct association between $\sigma$ values and blood flow states, enabling blood flow information to be extracted without correlation processing.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmological diagnosis method comprising the steps of:
   projecting a laser beam of prescribed diameter at a region of an eye to produce a laser speckle pattern formed by light scattered from tissues of the eye fundus;
   photoelectrically detecting movement of the laser speckle pattern through a detecting aperture as a fluctuation in the light intensity of the speckles to produce a speckle signal corresponding to the detected movement;
   measuring a photon correlation function of the speckle signal to determine a blood flow state in the eye fundus tissue from the measured photon correlation function;
   photoelectrically counting count data corresponding to the laser speckle pattern as photoelectric pulses per unit sampling time;
   storing the count data in a computer memory as time series data over a measurement time;
   dividing the stored count data by the unit sampling time; and
   processing the count data divided by the unit sampling time to calculate a variance for each of the count data and classifying the count data as blood vessel signal data, indeterminate signal data, or surrounding tissue signal data by comparing the calculated variance with two reference values.

2. An ophthalmological diagnosis method as set forth in claim 1, wherein a correlation function is calculated for each of the count data divided by the unit sampling time.

3. An opthalmological diagnosis method as set forth in claim 1, wherein a correlation time is calculated for each of the count data divided by the unit sampling time.

4. An opthalmological diagnosis method as set forth in claim 3, wherein the inverse of the correlation time obtained per unit sampling time is sequentially displayed per unit sampling time.

5. An ophthalmological diagnosis method as set forth in claim 3, wherein the count data are grouped according to the calculated correlation time.

6. An ophthalmological diagnosis method as set forth in claim 1, wherein the count data are grouped according to the calculated variance.

7. An ophthalmological diagnosis method as set forth in claim 6, wherein the photon correlation function is obtained for each of the grouped count data.

8. An ophthalmological diagnosis method as set forth in the claim 1, wherein the variance calculated per unit sampling time is sequentially displayed per unit sampling time as time-series data.

* * * * *